United States Patent
Sugiura et al.

(10) Patent No.: US 9,512,276 B2
(45) Date of Patent: Dec. 6, 2016

(54) PHENOL-MODIFIED POLYORGANOSILOXANE WITH REDUCED PLATINUM CONTENT, METHOD FOR PREPARING THE SAME, AND MODIFIER FOR ORGANIC RESIN CONTAINING THE SAME

(71) Applicant: Dow Corning Toray Co., Ltd., Tokyo (JP)

(72) Inventors: Tsunehito Sugiura, Ichihara (JP); Yasunori Chayama, Ichihara (JP); Masashi Matsuba, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/440,924

(22) PCT Filed: Nov. 7, 2013

(86) PCT No.: PCT/JP2013/080107
§ 371 (c)(1),
(2) Date: May 6, 2015

(87) PCT Pub. No.: WO2014/073605
PCT Pub. Date: May 15, 2014

(65) Prior Publication Data
US 2015/0291738 A1    Oct. 15, 2015

(30) Foreign Application Priority Data

Nov. 7, 2012 (JP) .................... 2012-245338

(51) Int. Cl.

| | | |
|---|---|---|
| C08G 77/38 | (2006.01) | |
| C08G 64/18 | (2006.01) | |
| C08L 83/04 | (2006.01) | |
| C08L 83/06 | (2006.01) | |
| C07F 7/08 | (2006.01) | |
| C08G 64/42 | (2006.01) | |

(52) U.S. Cl.
CPC .............. *C08G 77/38* (2013.01); *C07F 7/0852* (2013.01); *C07F 7/0879* (2013.01); *C08G 64/18* (2013.01); *C08G 64/186* (2013.01); *C08G 64/42* (2013.01); *C08L 83/04* (2013.01); *C08L 83/06* (2013.01); *C08K 2201/019* (2013.01)

(58) Field of Classification Search
CPC ... C08G 77/448; C08G 64/186; C08G 64/28
See application file for complete search history.

(56) References Cited

U.S. PATENT DOCUMENTS

| | | | |
|---|---|---|---|
| 5,204,438 A | | 4/1993 | Snow et al. |
| 5,502,134 A | * | 3/1996 | Okamoto ............ C08G 64/186 524/537 |
| 5,541,278 A | | 7/1996 | Raleigh et al. |
| 6,492,481 B1 | | 12/2002 | Davis et al. |
| 7,998,416 B2 | | 8/2011 | Hartmann-Thompson |
| 8,981,017 B2 | | 3/2015 | Ishikawa |
| 2003/0065122 A1 | | 4/2003 | Davis |
| 2005/0090015 A1 | | 4/2005 | Hartmann-Thompson |
| 2008/0210129 A1 | | 9/2008 | Nienstedt et al. |
| 2009/0263287 A1 | | 10/2009 | Hartmann-Thompson |
| 2010/0209301 A1 | | 8/2010 | Hartmann-Thompson |
| 2012/0283393 A1 | | 11/2012 | Ishikawa |

FOREIGN PATENT DOCUMENTS

| | | |
|---|---|---|
| CN | 102652149 A | 8/2012 |
| EP | 0 433 746 A2 | 6/1991 |
| EP | 0 668 137 A2 | 8/1995 |
| EP | 1 029 888 A1 | 8/2000 |
| EP | 1 529 804 A1 | 5/2005 |
| EP | 2 511 321 A1 | 10/2012 |
| JP | H 03-79626 A | 4/1991 |
| JP | H 04-120132 A | 4/1992 |
| JP | H 05-156019 A | 6/1993 |
| JP | H 06-184310 A | 7/1994 |
| JP | H 07-033859 A | 2/1995 |
| JP | H 07-238170 A | 9/1995 |

(Continued)

OTHER PUBLICATIONS

International Search Report for Application No. PCT/JP2013/080107 dated Dec. 24, 2013, 5 pages.
English language abstract for CN 102652149 extracted from espacenet.com database on May 14, 2015, 1 page.
English language abstract for JPH 03-79626 extracted from espacenet.com database on May 14, 2015, 2 pages.
English language abstract for JPH 04-120132 extracted from espacenet.com database on May 14, 2015, 2 pages
English language abstract and machine-assisted English translation for JPH 05-156019 extracted from espacenet.com database on May 14, 2015, 13 pages.

(Continued)

*Primary Examiner* — Kuo-Liang Peng
(74) *Attorney, Agent, or Firm* — Howard & Howard Attorneys PLLC

(57) ABSTRACT

A phenol-modified polyorganosiloxane suitable as a modifier for an organic resin, in which a platinum metal content is reduced, and the yellowing is reduced, a method for preparing the same, and a modifier for an organic resin containing the same are provided. The phenol-modified polyorganosiloxane is a compound of formula (I), having a platinum metal content of 0.9 ppm or less. The phenol-modified polyorganosiloxane can be prepared by subjecting a phenol compound substituted with an alkenyl group of formula (IV) and a polyorganohydrogen siloxane of formula (V) to a hydrosilation reaction in the presence of a platinum-based catalyst applicable to a homogenous system, and subsequently, reducing the platinum metal content of the resulting product to 0.9 ppm or less by conducting one or more filtration procedures selected from the group consisting of filtration conducted where activated carbon is added, filtration conducted by using a filter comprising activated carbon, and filtration conducted by using a filter capable of adsorbing cations, alone or in combination.

13 Claims, No Drawings

(56) References Cited

FOREIGN PATENT DOCUMENTS

| JP | 3831834 B | 11/1997 |
|---|---|---|
| JP | H 10-017670 A | 1/1998 |
| JP | H 10-182832 A | 7/1998 |
| JP | 2000-080192 A | 3/2000 |
| JP | 2000-080279 A | 3/2000 |
| JP | 2001-147544 A | 5/2001 |
| JP | 2005-134392 A | 5/2005 |
| JP | 2011-122048 A | 6/2011 |
| KR | 10-2012-0098769 A | 9/2012 |
| WO | WO 99/24509 A1 | 5/1999 |
| WO | WO 02/04545 A1 | 1/2002 |
| WO | WO 2011/071128 A1 | 6/2011 |
| WO | WO 2013/066983 A1 | 5/2013 |

OTHER PUBLICATIONS

English language abstract for JPH 06-184310 extracted from espacenet.com database on May 14, 2015, 2 pages.

English language abstract and machine-assisted English translation for JPH 07-033859 extracted from PAJ database on May 14, 2015, 20 pages.

English language abstract and machine-assisted English translation for JPH 07-238170 extracted from espacenet.com database on May 14, 2015, 21 pages.

Machine-assisted English translation for JP 3831834 extracted from PAJ database on May 14, 2015, 81 pages.

English language abstract and machine-assisted English translation for JPH 10-017670 extracted from PAJ database on May 14, 2015, 20 pages.

English language abstract and machine-assisted English translation for JPH 10-182832 extracted from espacenet.com database on May 14, 2015, 70 pages.

English language abstract for JP 2000-080192 extracted from espacenet.com database on May 14, 2015, 1 page.

English language abstract for JP 2000-080279 extracted from espacenet.com database on May 14, 2015, 1 page.

English language abstract and machine-assisted English translation for JP 2001-147544 extracted from espacenet.com database on May 14, 2015, 73 pages.

English language abstract for JP 2005-134392 extracted from espacenet.com database on May 14, 2015, 1 page.

English language abstract for JP 2011-122048 extracted from espacenet.com database on May 14, 2015, 1 page.

English language abstract for KR 10-2012-0098769 extracted from espacenet.com database on May 14, 2015, 1 page.

English language abstract for WO 99/24509 extracted from espacenet.com database on May 14, 2015, 1 page.

English language abstract for WO 2011/071128 extracted from espacenet.com database on May 14, 2015, 1 page.

\* cited by examiner

PHENOL-MODIFIED POLYORGANOSILOXANE WITH REDUCED PLATINUM CONTENT, METHOD FOR PREPARING THE SAME, AND MODIFIER FOR ORGANIC RESIN CONTAINING THE SAME

RELATED APPLICATIONS

This application is the National Stage of International Patent Application No. PCT/JP2013/080107, filed on Nov. 7, 2013, which claims priority to and all the advantages of Japanese Patent Application No. 2012-245338, filed on Nov. 7, 2012, the content of which is incorporated herein by reference.

TECHNICAL FIELD

The present invention relates to a phenol-modified polyorganosiloxane characterized by reducing a platinum metal content, and a method for preparing the same, as well as a modifier for an organic resin, containing the phenol-modified polyorganosiloxane mentioned above.

BACKGROUND ART

It is known that a phenol-modified polyorganosiloxane can be used as an optical material such as contact lenses by utilizing a high refractive index thereof (for example, the section of Prior Art described in Japanese Unexamined Patent Application, First Publication No. H06-184310). In addition, it is known that a phenol-modified silicone oil can be used as a modifier for an aromatic polycarbonate resin (for example, Japanese Unexamined Patent Application, First Publication No. H10-182832 and Japanese Unexamined Patent Application, First Publication No. 2001-147544). Japanese Unexamined Patent Application, First Publication No. H10-182832 describes that a phenol-modified polyorganosiloxane having a phenolic functional group at the terminal of the molecular chain can be used as a modifier for an organic resin such as a polyester resin, a polyamide resin, a polycarbonate resin, and a polysulfone resin (the section of Prior Art).

In addition, Japanese Unexamined Patent Application, First Publication No. H03-79626 describes a polycarbonate resin modified by incorporating a phenol-modified polyorganosiloxane in the main chain of a polycarbonate resin.

In addition, in a method for preparing an organomodified polyorganosiloxane other than a phenol-modified polyorganosiloxane, it is known that after carrying out an addition reaction between an olefin and a hydrosilane compound using a platinum catalyst, a step of removing impurities with activated carbon before a stripping step is applied (for example, Japanese Unexamined Patent Application, First Publication No. H10-017670, Japanese Unexamined Patent Application, First Publication No. H07-238170, and Japanese Unexamined Patent Application, First Publication No. H05-156019). However, they completely fail to focus on the amount of platinum or the platinum catalyst remaining in the products and the hue of the obtained products. Heretofore, reducing a platinum content contained in a phenol-modified polyorganosiloxane with activated carbon has not been described, and effects obtained due to the reduction of the platinum content in the case of using a phenol-modified polyorganosiloxane as a modifier for a resin are not known.

Namely, none of the aforementioned Japanese Unexamined Patent Application, First Publication No. H06-184310, Japanese Unexamined Patent Application, First Publication No. H03-79626, Japanese Unexamined Patent Application, First Publication No. H10-182823, and Japanese Unexamined Patent Application, First Publication No. 2001-147544 describe or suggest that a content of platinum and a platinum catalyst remaining in a phenol-modified polyorganosiloxane and hue of the phenol-modified polyorganosiloxane as a product are focused on and controlled.

PRIOR ART DOCUMENTS

Patent Documents

[Patent Document 1] Japanese Unexamined Patent Application, First Publication No. H03-79626
[Patent Document 2] Japanese Unexamined Patent Application, First Publication No. H06-184310
[Patent Document 3] Japanese Unexamined Patent Application, First Publication No. H10-182832
[Patent Document 4] Japanese Unexamined Patent Application, First Publication No. 2001-147544
[Patent Document 5] Japanese Unexamined Patent Application, First Publication No. H10-017670
[Patent Document 6] Japanese Unexamined Patent Application, First Publication No. H07-238170
[Patent Document 7] Japanese Unexamined Patent Application, First Publication No. H05-156019

DISCLOSURE OF INVENTION

Technical Problems

However, in the case of modifying an organic resin such as a polycarbonate using a phenol-modified polyorganosiloxane, yellowing of the obtained polyorganosiloxane-modified polycarbonate resin was observed in some cases. In addition, a phenol-modified polyorganosiloxane, per se, was colored into yellow depending on the preparation conditions thereof, and was not preferable as a raw material for modifying a polycarbonate resin in some cases. The inventors of the present application carried out intensive studies on a phenol-modified polyorganosiloxane used in order to modify an organic resin such as a polycarbonate resin, which has hue in which yellow color is suppressed and a method for preventing the yellowing of a modified resin finally obtained, thus completing the present invention.

Technical Solution

That is, the inventors of the present application focused on the amount of platinum metal remaining in a phenol-modified polyorganosiloxane, and discovered that by preparing a phenol-modified polyorganosiloxane while controlling the platinum metal content of the phenol-modified polyorganosiloxane to be 0.9 ppm or less, and in particular, in a range of from 0.1 to 0.9 ppm, and preferably in a range of from 0.2 to 0.7 ppm based on the total mass of the phenol-modified polyorganosiloxane, a degree of yellowing of a silicone-modified organic resin prepared using the phenol-modified polyorganosiloxane can be reduced. In addition, the inventors of the present application discovered that by reducing a platinum metal content remaining in a phenol-modified polyorganosiloxane, a phenol-modified polyorganosiloxane in which a b* value measured by an L*a*b* color system is 1.10 or less, and that by using the phenol-modified polyorganosiloxane having such a b* value, a silicone-modified organic resin having preferable hue in which a yellow color is suppressed can be obtained. In addition, the inventors of the present application discovered that, as a method for reducing a platinum metal content contained in a phenol-modified polyorganosiloxane, a platinum-based catalyst capable of being used in a homogeneous system (in particular, one or more platinum-based catalysts selected from the group consisting of chloroplatinic acid, complexes of platinum with vinylsiloxanes, and platinum-olefin complexes) is used as a catalyst for an addition reaction between a phenol-based compound having an olefinic unsaturated group and a polyorganohydrogensiloxane, and the obtained reaction product is subjected to one or more filtration procedures selected from the group consisting of filtration with activated carbon, filtration with an activated carbon-containing filter, and filtration with a filter capable of adsorbing cations, alone and/or in combination, and thereby, the platinum metal content in the product can be remarkably reduced. Thereby, a method for preparing a phenol-modified polyorganosiloxane of the present invention was completed. In addition, by controlling the amount of a phenol compound substituted with an alkenyl group (for example, allylphenol) remaining in a phenol-modified polyorganosiloxane to 500 ppm or less, and preferably 450 ppm or less, a method for producing a phenol-modified polyorganosiloxane of the present invention, in which coloration or the like can be further reduced, was completed.

That is, the present invention provides a phenol-modified polyorganosiloxane in which a platinum metal content is reduced, more preferably a phenol-modified polyorganosiloxane having a reduced b* value, a method for preparing the same, a method for preventing yellowing of an organic resin, using the phenol-modified polyorganosiloxane mentioned above, a modifier for an organic resin, which comprises the phenol-modified polyorganosiloxane mentioned above, and a silicone-modified organic resin containing the phenol-modified polyorganosiloxane mentioned above, and in particular, a silicone-modified polycarbonate resin.

According to a first mode of the present invention, a phenol-modified polyorganosiloxane is provided, which is represented by the following formula (I), and has a platinum metal content of 0.9 ppm or less, and in particular, ranging from 0.1 to 0.9 ppm, and preferably ranging from 0.2 to 0.7 ppm.

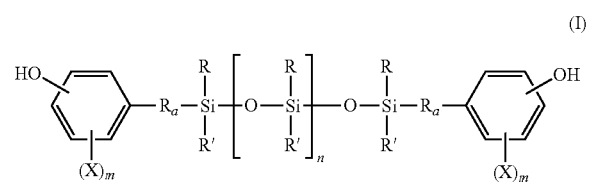

(I)

wherein each $R_a$ independently represents a substituted or unsubstituted, and linear, branched or cyclic alkylene moiety; and $R_a$ is a substituted or unsubstituted C2-C20 alkylene moiety;

R and R' are identical or different from one another, and each R and R' independently represents a group selected from the group consisting of C1-C20 alkyl or halogenated alkyl groups and substituted or unsubstituted C6-C20 aryl groups;

each X independently represents a substituent selected from the group consisting of substituted or unsubstituted C1-C20 linear, branched or cyclic alkyl groups; substituted or unsubstituted C6-C20 aryl groups; substituted or unsubstituted C6-C20 aryl C1-C20 alkyl groups (that is aralkyl group); substituted or unsubstituted C1-C20 alkyloxy groups; substituted or unsubstituted C6-C20 aryloxy groups; substituted or unsubstituted C6-C20 aryl C1-C20 alkyloxy groups; and halogen atoms;

each m independently represents an integer ranging from 0 to 4;

n is a number ranging from 5 to 500, in particular, ranging from 5 to 300, preferably ranging from 10 to 150, and more preferably ranging from 50 to 100; and the substitution positions of the OH groups on the phenyl groups at both terminals of the molecule are each independently ortho, meta, or para position.

In addition, the compound represented by the aforementioned formula (I) is preferably a phenol-modified polyorganosiloxane having a platinum metal content of 0.9 ppm or less, in particular, ranging from 0.1 to 0.9 ppm, and preferably ranging from 0.2 to 0.7 ppm, and represented by the following formula (II):

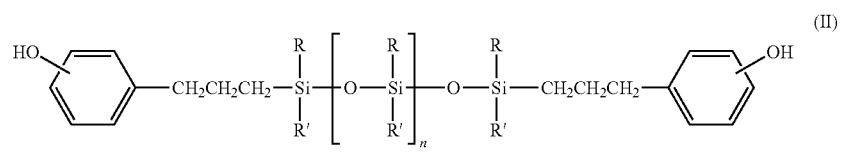

(II)

wherein each R and R' independently represents a group selected from the group consisting of a methyl group, a phenyl group and a naphthyl group; n is a number ranging from 5 to 500, in particular, ranging from 5 to 300, preferably ranging from 10 to 150, and more preferably ranging from 50 to 100; and each of the OH groups on the phenyl rings at the terminals of the molecule independently represents o-OH, m-OH, or p-OH group.

In addition, the compound represented by the aforementioned formula (I) is preferably a phenol-modified polyorganosiloxane in particular represented by the following formula (III), which has a platinum metal content of 0.9 ppm or less, particularly ranging from 0.1 to 0.9 ppm, and preferably ranging from 0.2 to 0.7 ppm.

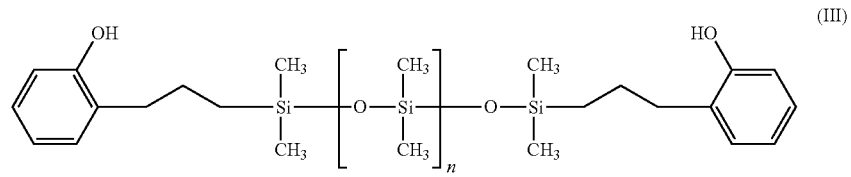

(III)

In formula (III), n is a number ranging from 5 to 500, in particular, ranging from 5 to 300, preferably ranging from 10 to 150, and more preferably ranging from 50 to 100.

In addition, in the present invention, the phenol-modified polyorganosiloxanes represented by the aforementioned formulae (I) to (III) preferably have a b* value of 1.10 or less measured by the L*a*b* color system defined in JIS Z 8729. By carrying out quality control of a product so as to set the b* value of the phenol-modified polyorganosiloxane of the present invention to 1.10 or less, in the case of using the polyorganosiloxane as a modifier for a resin, a modified resin with reduced yellowing or reduced coloring can be obtained. In addition, the phenol-modified polyorganosiloxanes represented by the aforementioned formulae (I) to (III) have a content of a phenol compound substituted with an alkenyl group (preferably allylphenol) represented by the following formula (IV) which is preferably 500 ppm or less, and in particular, preferably 450 ppm or less. When the amount of the phenol compound substituted with an alkenyl group represented by the following formula (IV) contained in the phenol-modified polyorganosiloxane exceeds 500 ppm, the amount is preferably reduced to 500 ppm or less by carrying out an operation for reducing the amount thereof, as described below, since an increased amount of the phenol compound substituted with an alkenyl group may cause coloration of the obtained phenol-modified polyorganosiloxane, and for this reason, this is not preferable.

Furthermore, the present invention provides a method for preparing a phenol-modified polyorganosiloxane which has a platinum metal content of 0.9 ppm or less, particularly ranging from 0.1 to 0.9 ppm, and preferably ranging from 0.2 to 0.7 ppm. The method includes the following steps of:

conducting a hydrosilation reaction between a phenol compound substituted with an alkenyl group, which is represented by the following formula:

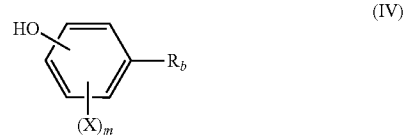

(IV)

wherein X and m are as defined in formula (I); $R_b$ represents an alkenyl group which is capable of producing the $R_a$ moiety defined in formula (I) by the addition reaction with a polyorganohydrogensiloxane represented by formula (V) shown below, and a polyorganohydrogensiloxane represented by the following formula (V):

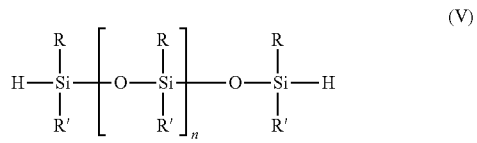

(V)

wherein R, R', and n are as defined above,
in the presence of a platinum-based catalyst applicable to a homogeneous system (in particular, one or more platinum-based catalysts selected from the group consisting of chloroplatinic acid, complexes of platinum with vinylsiloxanes, and platinum-olefin complexes) in an amount of more than 0.9 ppm as platinum metal; and reducing the platinum metal content of the resulting addition reaction product to 0.9 ppm or less, particularly a range of from 0.1 to 0.9 ppm, and preferably a range of from 0.2 to 0.7 ppm by conducting one or more filtration procedures selected from the group consisting of filtration which is conducted where activated carbon is added, filtration which is conducted by using a filter comprising activated carbon, and filtration which is conducted by using a filter capable of adsorbing cations, alone or in combination. Considering the industrial production scale of the aforementioned hydrosilation reaction product and the period of time required for the reaction step, the amount of the platinum-based catalyst used as a catalyst for the aforementioned hydrosilation reaction is generally (commonly) 1.5 ppm or more, or 2.0 ppm or more, based on a platinum metal amount. If the amount is below 1.5 ppm, the period of time required for the reaction step is extremely increased, and it may be difficult to industrially use the process.

Activated carbon, a filter containing activated carbon, and a filter capable of adsorbing cations used in the method of the present invention are not limited to specified ones.

In the preparation method mentioned above, after a hydrosilation-reaction product is subjected to one or more filtration procedures selected from the group consisting of filtration which is conducted where activated carbon is added, filtration which is conducted by using a filter comprising activated carbon, and filtration which is conducted by using a filter capable of adsorbing cations, alone or in combination, in the case where the unreacted compound of formula (IV) remains in the reaction product, a step of removing the unreacted compound of formula (IV) or reducing the amount thereof, such as conducting adsorption filtration using an adsorbent and/or stripping, is preferably carried out. The phenol compound substituted with an alkenyl group (preferably allylphenol) represented by the aforementioned formula (IV) may cause coloration of a product, and for this reason, a degree of removing the same is preferably 500 ppm or less, and in particular, preferably 450 ppm or less, based on the total amount.

In addition, the present invention provides a silicone-modified organic resin, such as a silicone-modified aromatic polycarbonate resin, which is modified with the aforementioned phenol-modified polyorganosiloxane having the platinum metal content of 0.9 ppm or less, particularly ranging from 0.1 to 0.9 ppm, and preferably ranging from 0.2 to 0.7 ppm. The silicone-modified organic resin is characterized in that a degree of yellowing is reduced, as compared with that in the case of using a phenol-modified polyorganosiloxane with the platinum metal content exceeding 0.9 ppm.

In addition, the present invention provides use of any one of the aforementioned phenol-modified polyorganosiloxanes, which have the platinum metal content of 0.9 ppm or less, particularly ranging from 0.1 to 0.9 ppm, and preferably ranging from 0.2 to 0.7 ppm, as a modifier in order to reduce the yellowing of an aromatic polycarbonate resin composition. In particular, the present invention provides a method for reducing the yellowing of a resulting silicone-modified aromatic polycarbonate resin by carrying out the modification of the aromatic polycarbonate resin using the phenol-modified polyorganosiloxane, which has the platinum metal content of 0.9 ppm or less, particularly ranging from 0.1 to 0.9 ppm, and preferably ranging from 0.2 to 0.7 ppm.

In addition the present invention provides a modifier for an organic resin, and particularly an aromatic polycarbonate resin, comprising the aforementioned phenol-modified polyorganosiloxane which has the platinum metal content of 0.9 ppm or less, particularly ranging from 0.1 to 0.9 ppm, and preferably ranging from 0.2 to 0.7 ppm. In the modification of an aromatic polycarbonate resin, by using the phenol-modified polyorganosiloxane of the present invention as a modifier, an advantage of improving impact resistance of the resin at a low temperature is achieved. In addition, the modifier of the present invention can also be used for particularly improving the water-repellent property and/or improving the mold-releasing property of an organic resin.

Effects of the Invention

In accordance with the preparation method according to the present invention, a phenol-modified polyorganosiloxane, which has the platinum metal content of 0.9 ppm or less, particularly ranging from 0.1 to 0.9 ppm, and preferably ranging from 0.2 to 0.7 ppm, can be obtained on an industrial scale. In the case of using such a phenol-modified polyorganosiloxane as a modifier for an organic resin, an effect of obtaining a silicone-modified organic resin composition and a resin-molded product with reduced yellowing or reduced coloration can be obtained. In addition, the presence or absence of the yellowing or a degree of the yellowing and coloration of the finally obtained silicone-modified organic resin composition or resin-molded product can be predicted by measuring the platinum metal content contained in the phenol-modified polyorganosiloxane, and in particular, measuring a b* value in the hue, if necessary. For this reason, they are helpful for the quality control of the products. The phenol-modified polyorganosiloxane of the present invention is useful as a modifier for modifying an organic resin used in, for example, an adhesive, coating, a FRP-molded product, a rubber blending agent and the like, as well as a modifier for modifying a cyanate ester or modifying a plastic such as a polycarbonate or the like.

BEST MODE FOR CARRYING OUT THE INVENTION

Hereinafter, the present invention is described in detail.
Phenol-Modified Polyorganosiloxane
The phenol-modified polyorganosiloxane of the present invention is represented by the following formula (I):

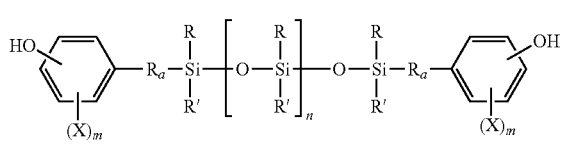

(I)

In formula (I), each $R_a$ independently represents a substituted or unsubstituted, and linear, branched or cyclic alkylene moiety. In addition, $R_a$ preferably represents a substituted or unsubstituted C2-C20 alkylene moiety, more preferably a substituted or unsubstituted C2-C12 alkylene moiety, and in particular, preferably a substituted or unsubstituted C3-C8 alkylene moiety. In the case of the alkylene moiety having a substituent, examples of the substituent include, for example, a halogen group such as fluorine, chlorine or the like, and an aryl group such as phenyl, tolyl or the like. As $R_a$, examples of particularly preferable moieties include a propylene moiety, an isopropylene moiety, a butylene moiety and an isobutylene moiety.

In formula (I), R and R' may be identical or different from one another, and each R and R' independently represents a group selected from the group consisting of C1-C20 alkyl or halogenated alkyl groups and substituted or unsubstituted C6-C20 aryl groups. The halogenated alkyl group can be mono- or polyhalogenated, and it may be a perhalogenated alkyl group. Halogen is preferably fluorine or chlorine, and in particular, fluorine is preferable. Examples of substituents other than halogen include those described as the substituent for an alkylene group. Preferable examples of R and R' include a methyl group, a phenyl group, and a naphthyl group.

The independent substituted phenyl groups at both terminals of formula (I) may optionally have substituents X other than a hydrogen atom, in addition to the OH groups shown in the chemical formula. The number m of the substituents X for the independent substituted phenyl groups is an integer ranging from 0 to 4. Each X independently represents a group selected from the group consisting of substituted or unsubstituted C1-C20 linear, branched or cyclic alkyl groups; substituted or unsubstituted C6-C20 aryl groups; substituted or unsubstituted C6-C20 aryl C1-C20 alkyl groups (that is aralkyl group); substituted or unsubstituted C1-C20 alkyloxy groups; substituted or unsubstituted C6-C20 aryloxy groups; substituted or unsubstituted C6-C20 aryl C1-C20 alkyloxy groups; and halogen atoms. Examples of the substituents therefor include those described as the substituents for the alkylene moiety $R_a$, such as a halogen group such as fluorine or the like. Therefore, one example of X is a halogenated alkyl group. The m of the aforementioned formula (I) is preferably 0.

In addition, the substitution positions of the OH groups on the hydroxyphenyl groups at both terminals of the formula (I) can be each independently ortho, meta, or para, and in particular, preferably ortho.

In the aforementioned formula (I), n represents a number of the organosiloxane units. The aforementioned n is not particularly limited, and generally ranges from 5 to 500, particularly ranges from 5 to 300, preferably ranges from 10 to 150, and more preferably ranges from 50 to 100. n represents an average value of the whole compound of formula (I). The same definition is applied to other chemical formulae described in the specification of the present application.

By setting n to 500 or less, there are advantages that the purification of a product by filtration and stripping of the unreacted raw materials if necessary can be easily carried out in the preparation steps for the aforementioned aryl-modified polyorganosiloxane, and a product with a high purity can be easily produced.

In one of the preferable modes, in the aforementioned formula (I), $R_a$ independently represents a moiety selected from the group consisting of propylene, isopropylene, and butylene; R and R' are independently selected from the group consisting of a methyl group, a phenyl group and a naphthyl group; X is a hydrogen atom; and n ranges from 5 to 500, particularly ranges from 5 to 300, preferably ranges from 10 to 150, and more preferably ranges from 50 to 100.

In addition, the aryl-modified polyorganosiloxane represented by the aforementioned formula (I) is preferably a compound represented by the following formula (II):

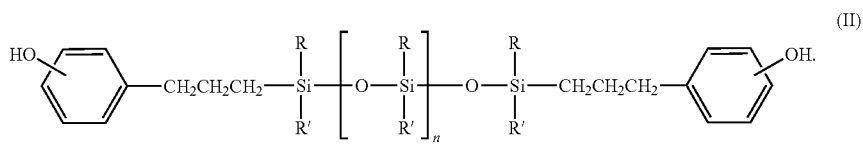

(II)

In the aforementioned formula (II), each R and R' independently represents a group selected from the group consisting of a methyl group, a phenyl group and a naphthyl group; n is the same as defined above for the formula (I); and each of OH groups on the phenyl groups at the terminals of the molecule independently represents an o-OH group, a m-OH group, or a p-OH group. R and R' are independently preferably selected from the group consisting of methyl and phenyl, and methyl is preferable therefor.

The particularly preferable compound of formula (I) is a phenol-modified polyorganosiloxane represented by the following formula (III):

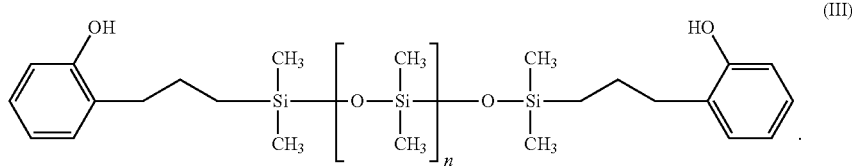

(III)

In formula (III), n ranges from 5 to 500, particularly ranges from 5 to 300, preferably ranges from 10 to 150, and more preferably ranges from 50 to 100.

As described above, the phenol-modified polyorganosiloxane of the present invention has a platinum metal content which is 0.9 ppm or less, particularly ranges from 0.1 to 0.9 ppm, and preferably ranges from 0.2 to 0.7 ppm. No phenol-modified polyorganosiloxane of formula (I) having such a reduced platinum metal content has been known heretofore. The inventors of the present application discovered that a phenol-modified polyorganosiloxane of formula (I) having a platinum metal content in the aforementioned range can be prepared by a preparation method described below. The amount of platinum metal is a value measured by means of ICP-MS (Inductively Coupled Plasma-Mass Spectrometry) (Model Number=Agilent 7500a, manufactured by Yokogawa Analytical Systems Inc.).

In addition, in the present invention, the phenol-modified polyorganosiloxanes represented by the aforementioned formulae (I) to (III) preferably have a b* value, measured by the L*a*b* color system, which is 1.10 or less. By controlling the platinum metal content contained therein to a range which is 0.9 ppm or less, in particular ranging from 0.1 to 0.9 ppm, and preferably ranging from 0.2 to 0.7 ppm, and at the same time, removing coloring materials other than platinum compounds by means of a known method including, for example, adsorbing these materials to an absorbent and filtering, the phenol-modified polyorganosiloxanes can be obtained. The L*a*b* color system is known in the art, and can be measured by means of a spectrophotometric colorimeter.

Method for Preparing Phenol-Modified Polyorganosiloxane

A method for preparing a phenol-modified polyorganosiloxane of the present invention is described below.

A phenol-modified polyorganosiloxane having a platinum metal content of 0.9 ppm or less can be generally prepared by means of a method including the steps of:

conducting a hydrosilation reaction between a phenol compound substituted with an alkenyl group, which is represented by the following formula (IV):

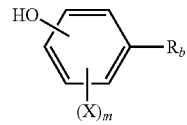

(IV)

wherein X and m are as defined in formula (I); $R_b$ represents an alkenyl group which is capable of producing the $R_a$ moiety defined in formula (I) by the addition reaction with a polyorganohydrogensiloxane represented by formula (V) shown below:

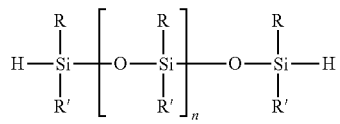

(V)

wherein R, R', and n are as defined in formula (I), in the presence of one or more platinum-based catalysts selected from the group consisting of chloroplatinic acid, complexes of platinum with vinylsiloxanes, and platinum-olefin complexes in an amount of more than 0.9 ppm, preferably 1.5 ppm or more, and in particular, 2.0 ppm or more, as platinum metal; and purifying the resulting hydrosilation reaction product by conducting one or more filtration procedures selected from the group consisting of filtration which is conducted where activated carbon is added, filtration which is conducted by using a filter comprising activated carbon, and filtration which is conducted by using a filter capable of adsorbing cations, alone or in combination; and if necessary, optionally removing impurities such as unreacted raw materials such as unreacted compound of formula (IV) and the like, such as a stripping step.

In the compound represented by the aforementioned formula (IV), $R_b$ is preferably a group selected from the group consisting of a 3-propenyl group, an isopropenyl group and a 4-butenyl group, and $R_b$ is in particular, preferably a 3-propenyl group. In addition, m of formula (IV) is in particular, preferably 0. Therefore, the formula (IV) is preferably

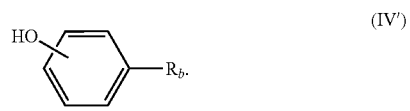

(IV')

The hydroxyl group of the formula (IV') may be any one of ortho-, meta-, or para-substituent with respect to $R_b$. A compound in which the hydroxyl group is at the ortho-position with respect to $R_b$ is in particular, preferable.

In the aforementioned formula (V), R and R' are as defined in the aforementioned formula (I), and each R and R' is independently preferably selected from the group consisting of a methyl group, a phenyl group, and a naphthyl group. R and R' are, in particular, preferably a methyl group. The n in formula (V) ranges from 5 to 500, in particular, ranges from 5 to 300, preferably ranges from 10 to 150, and more preferably ranges from 50 to 100. As described above, n is an average value of the entire compound.

The aforementioned compound of formula (IV) and compound of formula (V) are known compounds, or compounds which can be produced in accordance with a method for preparing known compounds can be used therefor.

Compounds of formulae (I) to (III) can be prepared by subjecting the compound of formula (IV) and the compound of formula (V) to addition reaction in the presence of a hydrosilation catalyst. A hydrosilation reaction between a compound containing an aliphatic unsaturated group and an Si—H-containing polyorganosiloxane is a known reaction, and a conventional hydrosilation reaction condition can also be used in the method for preparing a compound of formula (I) of the present invention. The method for preparing a compound of formula (I) of the present invention is characterized in that by using, as a hydrosilation catalyst, a platinum-based catalyst applicable to a homogeneous system (in particular, one or more platinum-based catalysts selected from the group consisting of chloroplatinic acid, complexes of platinum with vinylsiloxanes, and platinum-olefin complexes) in an amount of more than 0.9 ppm as a platinum metal content in the un-purified hydrosilation reaction product; and at the same time, by conducting one or more filtration procedures selected from the group consisting of filtration which is conducted where activated carbon is added, filtration which is conducted by using a filter comprising activated carbon, and filtration which is conducted by using a filter capable of adsorbing cations, alone or in combination, the platinum metal content of the resulting addition reaction product is reduced to 0.9 ppm or less, particularly a range of from 0.1 to 0.9 ppm, and preferably a range of from 0.2 to 0.7 ppm. The inventors of the present application discovered that upon the purification of a crude product obtained by carrying out a hydrosilation reaction between a compound of formula (IV) and a compound of formula (V), one or more filtration procedures selected from the group consisting of filtration with activated carbon, filtration with a filter including activated carbon, and filtration with a filter capable of adsorbing cations, alone or in combination, are carried out, and thereby, the platinum metal content of the resulting addition reaction product can be reduced to 0.9 ppm or less. That is, the filtration step of the present invention can be carried out by one or more filtration procedures selected from the three types mentioned above, alone or in combination. Here, in the case of using chloroplatinic acid as the hydrosilation reaction catalyst, the platinum content can be effectively reduced by conducting the filtration using a filter including activated carbon, and for this reason, the hydrosilation reaction catalyst to be used is, in particular, preferably chloroplatinic acid. Even if a platinum-based catalyst applicable to another homogeneous system such as tetramethyldivinyldisiloxane platinum complex or the like is used as a catalyst, the plural treatments of the aforementioned filtrations or the combination with two types of filters are carried out, and thereby, a platinum metal content in the obtained product can be reduced to 0.9 ppm or less. In view of increased efficacy of removing the platinum metal, the hydrosilation reaction product is in particular, preferably filtered using a filter containing activated carbon.

The hydrosilation catalyst used in the present invention is preferably a platinum catalyst applicable to a homogenous system reaction, in view of the purification of a crude product obtained by conducting a hydrosilation reaction between a compound of the aforementioned formula (IV) and a compound of the aforementioned formula (V). Chloroplatinic acid, a complex of platinum with a vinylsiloxane, and a platinum-olefin complex are more preferable. A platinum-alkenylsiloxane complex such as a complex of chloroplatinic acid and tetramethyldivinyldisiloxane, a complex of chloroplatinic acid and tetramethyltetravinylcyclotetrasiloxane, a platinum-tetramethyldivinyldisiloxane complex, platinum-tetramethyltetravinylcyclotetrasiloxane complex, or the like, as well as chloroplatinic acid are, in particular, preferable. As the particularly preferable hydrosilation catalyst used in the present invention, a tetramethyldivinyldisiloxane-platinum complex or chloroplatinic acid is the most preferable. The aforementioned platinum complexes can be used alone or in combination of two or more types.

After the hydrosilation reaction between the compound of formula (IV) and the compound of formula (V) is carried out, and subsequently, the obtained crude product is subjected to one or more filtration procedures selected from the group consisting of filtration which is conducted where activated carbon is added, filtration which is conducted by using a filter comprising activated carbon, and filtration which is conducted by using a filter capable of adsorbing cations, alone or in combination, impurities such as an unreacted compound of formula (IV) remaining in the reaction product are more preferably removed, if necessary. That is, as the aforementioned filtration, one type of the aforementioned filtration procedures may be conducted once or more; two or more types of the aforementioned procedures may be conducted once or more respectively; or the combination filtration of the two or more types of the aforementioned procedures may be conducted once. For example, a procedure of combining the use of activated carbon and the use of a filter containing activated carbon or a filter capable of adsorbing cations can be conducted. Also, the filtration procedure may be carried out by using a combination of a filter containing activated carbon and a filter capable of adsorbing cations. In addition, a procedure of conducting a combination of plural filtration procedures once and a filtration procedure of any one type of the filtration procedures can be conducted respectively once or more. All the cases are within the scope of the present invention. A procedure for removing impurities is not limited to a specified procedure. Preferable examples thereof include a stripping operation in which impurities are removed from the product under reduced pressure with heating. In the case of the compound of formula (I) containing a large amount of the compound of formula (IV) as impurities, the yellowing of a silicone-modified organic resin obtained by using the compound of formula (I) as a raw material for modifying an organic resin such as an aromatic polycarbonate, that is, a modifier, may be caused. In view of prevention of the yellowing of the finally obtained silicone-modified organic resin, the amount of the unreacted compound of formula (IV) contained in the compound of formula (I) is preferably 600 ppm or less, more preferably 550 ppm or less, and in particular, preferably 500 ppm or less. In a common addition reaction, there is a case of the unreacted phenol compound substituted with an alkenyl group represented by formula (IV) remaining in an amount of about 5,000 ppm. However, in accordance with the method of the present invention, the impurities can be easily reduced to 500 ppm or less.

In addition, the step of removing impurities such as the unreacted compound of formula (IV) and the like is preferably conducted after the step of the purification by conducting one or more filtration procedures selected from the group consisting of filtration which is conducted where activated carbon is added, filtration which is conducted by using a filter comprising activated carbon, and filtration which is conducted by using a filter capable of adsorbing cations, alone or in combination. The inventors of the present application discovered that in the case of conducting the step of removing the unreacted compound of formula (IV) after subjecting the hydrosilation reaction product to a purification treatment using a filter containing activated carbon or the like as described above, the platinum metal content contained in the product can be easily reduced to the desirable level, as compared with the case of conducting the aforementioned steps in reverse. The step of removing the unreacted compound of formula (IV) from the reaction product can be conducted in accordance with any known procedure. Examples thereof include adsorption to an adsorbent and filtration, stripping under reduced pressure with heating, and the like. In particular, a stripping operation is preferable.

Usage of Phenol-Modified Polyorganosiloxane

The phenol-modified polyorganosiloxane of the present invention can be used as a material for modifying an organic resin. Types of the organic resins are not particularly limited. Examples of the organic resins include, for example, a polyester resin, a polyamide resin, a polycarbonate resin, a polysulfone resin, a phenol resin, a cyanate ester and the like. In particular, in the case of the phenol group which the compound of the present invention has being possible to react with the organic resin, or in the case of the compound of the present invention being possible to be incorporated into the molecular structure of the organic resin, the phenol-modified polyorganosiloxane of the present invention can be used as a reactive modifier for an organic resin. By using the phenol-modified polyorganosiloxane of the present invention as an additive or a modifier for an organic resin, effects of improvement of a mold-processing property of the obtained organic resin, such as improvement of a mold-releasing property and/or a water-repellent property can be expected. In addition, examples of usage of the phenol-modified polyorganosiloxane of the present invention as an additive or a modifier include an adhesive, a coating, a FRP-molded product, a rubber-blending agent and the like.

In particular, the phenol-modified polyorganosiloxane of the present invention is useful as a modifier for an aromatic polycarbonate. Use of the phenol-modified polyorganosiloxane as a reactive modifier for an aromatic polycarbonate is described in, for example, Japanese Unexamined Patent Application, First Publication No. H03-79626 and Japanese Unexamined Patent Application, First Publication No. H10-182832. However, the aforementioned technical documents fail to describe that in order to suppress the yellowing of the obtained silicone-modified polycarbonate, the phenol-modified polyorganosiloxane in which a platinum metal content is reduced to 0.9 ppm or less is used as a modifier for an organic resin, and thereby, the yellowing of the obtained silicone-modified organic resin can be suppressed.

As detailed examples of a method for using the phenol-modified polyorganosiloxane of the present invention as a modifier for an aromatic polycarbonate, the following methods can be mentioned. However, the method is not limited thereto. For example, a silicone-modified aromatic polycarbonate can be prepared by using a phenol-modified polyorganosiloxane of the present invention, in addition to a known raw material for preparing an aromatic polycarbonate, such as a compound with two hydroxyphenyl groups having a skeleton of diphenylmethane such as bisphenol A and/or bisphenol F, by means of an ester exchange method using a carbonic ester or a phosgene method in the presence of an end-capping agent and/or a branching agent, if necessary. In addition, a silicone-modified aromatic polycarbonate can be prepared by polymerizing a compound with two hydroxyphenyl groups having a skeleton of diphenylmethane such as bisphenol A and/or bisphenol F by means of a phosgene method or the like to synthesize a phenol-terminated polymer or prepolymer, and connecting this polymer or prepolymer to the phenol-modified polyorganosiloxane of the present invention by using an acid-binding agent. As such a method, methods described in Japanese Unexamined Patent Application, First Publication No. H03-79626 and Japanese Unexamined Patent Application, First Publication No. H10-182832 or other known methods can be used. In addition, the raw materials for preparing an aromatic polycarbonate are not limited to bisphenol A and bisphenol F described above, and any known raw materials for preparing a polycarbonate, and a combination of the raw materials can be used.

An aromatic polycarbonate prepared by using the phenol-modified polyorganosiloxane of formula (I) of the present invention which has a platinum metal content of 0.9 ppm or less, preferably ranging from 0.1 to 0.9 ppm, and more preferably ranging from 0.2 to 0.7 ppm, as a modifier can exhibit an effect of hardly developing yellowing (or coloring), as compared with an aromatic polycarbonate prepared by using a phenol-modified polyorganosiloxane having a platinum metal content of greater than 0.9 ppm as a modifier. Such an effect is not limited for an aromatic polycarbonate, and can be expected to be exhibited even in the case of using the phenol-modified polyorganosiloxane of the present invention as a modifier for other organic resins such as a polyester resin, a polyamide resin, a polysulfone resin, a phenol resin, and a cyanate ester. By removing the platinum catalyst from the phenol-modified polyorganosiloxane, the great reduction of adverse effects on physical properties of the organic resins to be obtained using the phenol-modified polyorganosiloxane as a modifier can be sufficiently expected.

In addition, the present invention also provides a resin composition comprising an organic resin modified with the phenol-modified polyorganosiloxane of formula (I) having a platinum metal content of 0.9 ppm or less, and in particular, a silicone-modified aromatic polycarbonate resin, as well as a molded product obtained therefrom. In the aforementioned resin composition and molded product, the effect of the present invention of hardly causing yellowing can be obtained.

Therefore, the present invention also provides a method for using the phenol-modified polyorganosiloxane of formula (I) which has a platinum metal content in an amount of 0.9 ppm or less, particularly ranging from 0.1 to 0.9 ppm, and preferably ranging from 0.2 to 0.7 ppm as a modifier in order to reduce the yellowing of an organic resin composition and in particular, an aromatic polycarbonate resin composition, as well as a molded product obtained therefrom. In the case of using the phenol-modified polyorganosiloxane of formula (I) as a modifier, a method has not been known heretofore in which a platinum metal content contained in the modifier was focused on, and reduced to 0.9 ppm or less, to reduce the yellowing the obtained silicone-modified organic resin. In addition, the phenol-modified polyorganosiloxane of formula (I) has a b* value measured with the L*a*b* color system, which is preferably 1.10 or less. Therefore, the present invention also provides a modifier for an organic resin, and in particular, an aromatic polycarbonate, which is composed of the phenol-modified polyorganosiloxane of formula (I) having a platinum metal content of 0.9 ppm or less, in order to improve impact resistance at a low temperature, a water-repellent property and/or improve a mold-releasing property of the organic resin.

Hereinafter, the present invention is described based on Examples. It should be understood that the present invention is not limited to the following Examples.

EXAMPLES

A phenol-modified polyorganosiloxane of formula (III) was prepared as shown below, based on the following reaction scheme:

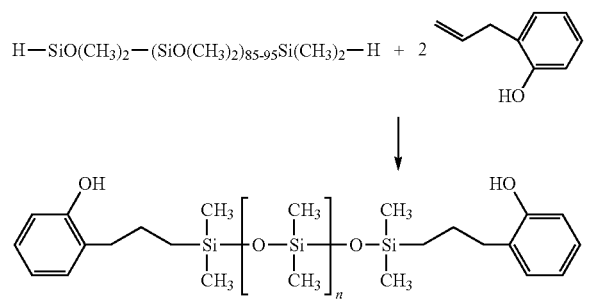

In the Examples and Comparative Examples described below, the amount of the platinum metal contained in the product corresponds to a value measured by means of ICP-MS (Inductively Coupled Plasma-Mass Spectrometry) (Model Number=Agilent 7500a, manufactured by Yokogawa Analytical Systems Inc.).

In addition, in the following Examples, the amount of the allylphenol remaining in the reaction product after the hydrosilation reaction was 5,000 ppm, but the amount was reduced to the range of from 400 to 500 ppm by means of a stripping treatment.

In addition, the platinum metal content contained in the product corresponds to a value measured by means of ICP-MS (Inductively Coupled Plasma-Mass Spectrometry) (Model Number=Agilent 7500a, manufactured by Yokogawa Analytical Systems Inc.).

Example 1

2-Allylphenol in an amount of 2.4 mol and chloroplatinic acid (a 5% by weight isopropyl alcohol solution) (2.4 ppm equivalent based on platinum) were added to a both-terminal-hydrogen polydimethylsiloxane in an amount of 1 mol (hydrogen %: 0.031) to react them for 2 hours at 120° C. After the absence of the remaining Si—H was confirmed by means of a hydrogen generation method with a water/ethanol/potassium hydroxide saturated solution, the reaction mixture was cooled to room temperature and was filtered once by means of an activated carbon-containing Zetacarbon filter R-55 (manufactured by Sumitomo 3M). Subsequently, unreacted 2-allylphenol was removed from the obtained product under reduced pressure for 3 hours at 150° C. The remaining platinum catalyst contained in the obtained product was reduced to 0.3 ppm as platinum metal, and the b* (yellowish) value measured by means of a colorimeter, Spectrophotometer CM-5 (manufactured by KONICA MINOLTA) was 0.47. The outer appearance of the obtained product was colorless.

Example 2

2-Allylphenol in an amount of 2.4 mol and chloroplatinic acid (a 5% by weight isopropyl alcohol solution) (2.4 ppm equivalent based on platinum) were added to a both-terminal-hydrogen polydimethylsiloxane in an amount of 1 mol (hydrogen %: 0.08) to react them for one hour at 120° C. After the absence of the remaining Si—H was confirmed by a degree of coloration using a saturated ethanol solution of silver nitrate, the reaction mixture was cooled to room temperature and was filtered 4 times by means of an activated carbon-containing Zetacarbon filter R-55 (manufactured by Sumitomo 3M). Subsequently, the unreacted 2-allylphenol was removed from the obtained product under reduced pressure for 3 hours at 150° C. The remaining platinum catalyst contained in the obtained product was reduced to 0.4 ppm as platinum, and the b* (yellowish) value measured by means of a colorimeter, Spectrophotometer CM-5 (manufactured by KONICA MINOLTA) was 0.8. The outer appearance of the obtained product was almost colorless.

Example 3

2-Allylphenol in an amount of 2.4 mol and a tetramethyldivinyldisiloxane platinum complex catalyst (a 5% by weight isopropyl alcohol solution) (2.4 ppm equivalent based on platinum) were added to a both-terminal-hydrogen polydimethylsiloxane in an amount of 1 mol (hydrogen %: 0.031) to react them for 2 hours at 120° C. After the absence of the remaining Si—H was confirmed by means of a hydrogen generation method with a water/ethanol/potassium hydroxide saturated solution, the reaction mixture was cooled to room temperature and was filtered once by means of an activated carbon-containing Zetacarbon filter R-55 (manufactured by Sumitomo 3M). Subsequently, the unreacted 2-allylphenol was removed from the obtained product under reduced pressure for 3 hours at 150° C. The remaining platinum catalyst contained in the obtained product was reduced to 0.9 ppm or less as platinum, and the b* (yellowish) value measured by means of a colorimeter, Spectrophotometer CM-5 (manufactured by KONICA MINOLTA) was 0.94. The outer appearance of the obtained product was almost colorless.

Example 4

2-Allylphenol in an amount of 2.4 mol and chloroplatinic acid (a 5% by weight isopropyl alcohol solution) (2.4 ppm equivalent based on platinum) were added to a both-terminal-hydrogen polydimethylsiloxane in an amount of 1 mol (hydrogen %: 0.031) to react them for 2 hours at 120° C. After the absence of the remaining Si—H was confirmed by means of a hydrogen generation method with a water/ethanol/potassium hydroxide saturated solution, the reaction mixture was cooled to room temperature and was filtered once by means of a ZetaPlus filter EC series GN020 (manufactured by Sumitomo 3M). Subsequently, the unreacted 2-allylphenol was removed from the obtained product under reduced pressure for 3 hours at 150° C. The remaining platinum catalyst contained in the obtained product was reduced to 0.9 ppm or less as platinum, and the b* (yellowish) value measured by means of a colorimeter, Spectrophotometer CM-5 (manufactured by KONICA MINOLTA) was 1.08. The outer appearance of the obtained product was almost colorless.

Comparative Example 1

In this Comparative Example 1, after the step of removing the unreacted 2-allylphenol under reduced pressure with heating (stripping step) was conducted, the product was filtered using a carbon filter containing activated carbon.

2-Allylphenol in an amount of 2.4 mol and chloroplatinic acid (a 5% by weight isopropyl alcohol solution) (2.4 ppm equivalent based on platinum) were added to a both-terminal-hydrogen polydimethylsiloxane in an amount of 1 mol (hydrogen %: 0.031) to react them for 2 hours at 120° C. After the absence of the remaining Si—H was confirmed by means of a hydrogen generation method with a water/ethanol/potassium hydroxide saturated solution, the unreacted 2-allylphenol was removed from the obtained product under reduced pressure for 3 hours at 150° C. The obtained reaction mixture was cooled to room temperature and was filtered once by means of an activated carbon-containing Zetacarbon filter R-55 (manufactured by Sumitomo 3M). The remaining platinum catalyst contained in the obtained product was present in an amount of 2 ppm as platinum, and the b* (yellowish) value measured by means of a colorimeter, Spectrophotometer CM-5 (manufactured by KONICA MINOLTA) was 2.58. The outer appearance of the obtained product was pale yellow to pale brown.

Comparative Example 2

A phenol-modified polyorganosiloxane was prepared by the same procedures as those described in Example 1 mentioned above, with the proviso that the product was filtered using a cellulose filter instead of a Zetacarbon filter R55 containing activated carbon. The remaining platinum catalyst contained in the obtained product was present in an amount of 2 ppm as platinum, and the b* (yellowish) value measured by means of a colorimeter, Spectrophotometer CM-5 (manufactured by KONICA MINOLTA) was 2.58. The outer appearance of the obtained product was pale yellow to pale brown.

Reference Example

While a solution obtained by dissolving 74 g of 2,2-bis (4-hydroxyphenyl)propane (that is, bisphenol A) in 550 mL of an aqueous solution of sodium hydroxide in a concentration of 6% by weight, and 250 mL of methylene chloride were being mixed and stirred, a phosgene gas was blown into the aforementioned solution under cooling at 20° C. at a rate of 950 mL/sec for 15 minutes. Subsequently, the reaction liquid was allowed to stand to separate an organic layer. Thereby, a solution of a polycarbonate oligomer of bisphenol A with chloroformate groups at the terminals of the molecule, having a degree of polymerization ranging from 2 to 5, dissolved in methylene chloride was obtained. The chemical structure, the degree of polymerization, and the terminal groups were confirmed by means of $^1$H-NMR, MS, and GPC. Methylene chloride was added to the solution of the obtained oligomer dissolved in methylene chloride to set the total amount to 450 mL, and subsequently, mixed with 150 mL of an aqueous solution of sodium hydroxide in a concentration of 8% by weight, and a polysiloxane (144.7 g) and 3.0 g of p-tert-butylphenol as a molecular weight control agent were added thereto. Subsequently, while the aforementioned mixed solution was vigorously being stirred, 2 mL of an aqueous solution of triethylamine in a concentration of 7% by weight was added thereto. The mixture was reacted by stirring for 1.5 hours at 28° C. After completion of the reaction, the reaction product was diluted with 1 L of methylene chloride, and washed successively twice with 1.5 L of water, once with 1 L of 0.01 N hydrochloric acid, and twice with 1 L of water. The organic layer was poured into methanol. The precipitated polymer was filtered and dried. Thereby, 218 g of a polycarbonate resin was obtained.

The chemical structure and the copolymerization composition of the obtained polycarbonate resin were determined by means of $^1$H-NMR and $^{29}$Si-NMR spectra. In accordance with $^1$H-NMR, the peak of a polysiloxane (peak assigned to methyl moieties on a siloxane backbone at 0 to 0.1 ppm) and the peaks of bisphenol A (1.7 ppm and 7.1 to 7.3 ppm) were observed. In addition, in accordance with $^{29}$Si-NMR, the peaks of a normal dimethylsiloxane (−21 ppm and 7.8 ppm by the chemical shifts using tetramethylsilane as a standard) were observed. From these analysis results, it can be seen that the obtained polycarbonate resin contains a phenol-modified siloxane.

INDUSTRIAL APPLICABILITY

The phenol-modified polyorganosiloxanes obtained in accordance with the present invention have a greatly reduced platinum content, and are free from coloration. For this reason, they are extremely useful as a modifier for modifying an organic resin used in adhesives, coating, FRP-molded products, rubber-blending agents, and the like, as well as a modifier for modifying plastics such as polycarbonate, and the like, and denaturing cyanate esters.

The invention claimed is:
1. A phenol-modified polyorganosiloxane represented by the following formula (I) and having a platinum metal content of 0.9 ppm or less:

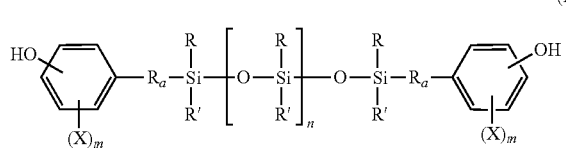

wherein each $R_a$ independently represents a substituted or unsubstituted, and linear, branched or cyclic alkylene moiety; and $R_a$ is a substituted or unsubstituted C2-C20 alkylene moiety;

R and R' are identical or different from one another, and each R and R' independently represents a group selected from the group consisting of C1-C20 alkyl or halogenated alkyl groups and substituted or unsubstituted C6-C20 aryl groups;

each X independently represents a substituent selected from the group consisting of substituted or unsubstituted C1-C20 linear, branched or cyclic alkyl groups; substituted or unsubstituted C6-C20 aryl groups; substituted or unsubstituted C6-C20 aryl C1-C20 alkyl groups (aralkyl groups); substituted or unsubstituted C1-C20 alkyloxy groups; substituted or unsubstituted C6-C20 aryloxy groups; substituted or unsubstituted C6-C20 aryl C1-C20 alkyloxy groups; and halogen atoms;

each m independently represents an integer ranging from 0 to 4;

n is a number ranging from 5 to 500; and the substitution positions of the OH groups on the phenyl groups at both terminals of the molecule are each independently ortho, meta, or para position.

2. The phenol-modified polyorganosiloxane according to claim 1, represented by the following formula (II) and having a platinum metal content of 0.9 ppm or less:

4. The phenol-modified polyorganosiloxane according to claim 3, having a platinum metal content of 0.9 ppm or less and having a b* value of 1.10 or less measured by the L*a*b* color system defined in JIS Z 8729.

5. The phenol-modified polyorganosiloxane according to claim 2, having a platinum metal content of 0.9 ppm or less and having a b* value of 1.10 or less measured by the L*a*b* color system defined in JIS Z 8729.

6. The phenol-modified polyorganosiloxane according to claim 1, having a platinum metal content of 0.9 ppm or less and having a b* value of 1.10 or less measured by the L*a*b* color system defined in JIS Z 8729.

7. A resin composition comprising an aromatic polycarbonate resin which is modified with the phenol-modified polyorganosiloxane according to claim 1.

8. A method comprising: using the phenol-modified polyorganosiloxane according to claim 1 as a modifier in order to reduce the yellowing of an aromatic polycarbonate resin composition.

9. A modifier for an organic resin comprising the phenol-modified polyorganosiloxane according to claim 1, wherein the modifier comprises platinum metal in an amount of 0.9 ppm or less.

10. The modifier of claim 9 for improving a water-repellent property or improving a mold-releasing property of the organic resin.

11. A method for preparing a phenol-modified polyorganosiloxane represented by the following formula (I) and having a platinum metal content of 0.9 ppm or less:

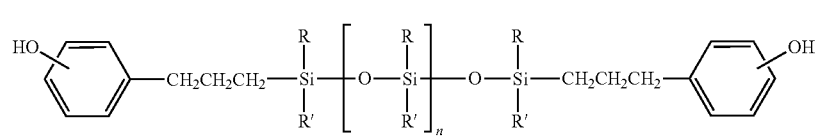

wherein each R and R' independently represents a group selected from the group consisting of a methyl group, a phenyl group and a naphthyl group; n is a number ranging from 5 to 500; and each phenyl group at the terminals of the molecule independently represents o-OH, m-OH, or p-OH group.

3. The phenol-modified polyorganosiloxane according to claim 2, represented by the following formula (III) and having a platinum metal content of 0.9 ppm or less:

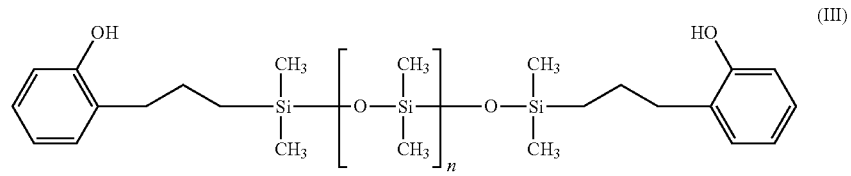

wherein n is a number ranging from 5 to 500.

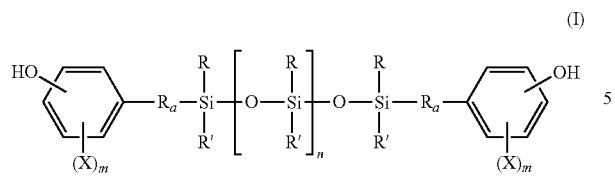

(I)

wherein each $R_a$ independently represents a substituted or unsubstituted, and linear, branched or cyclic alkylene moiety; and $R_a$ is a substituted or unsubstituted C2-C20 alkylene moiety;

R and R' are identical or different from one another, and each R and R' independently represents a group selected from the group consisting of C1-C20 alkyl or halogenated alkyl groups and substituted or unsubstituted C6-C20 aryl groups;

each X independently represents a substituent selected from the group consisting of substituted or unsubstituted C1-C20 linear, branched or cyclic alkyl groups; substituted or unsubstituted C6-C20 aryl groups; substituted or unsubstituted C6-C20 aryl C1-C20 alkyl groups (aralkyl groups); substituted or unsubstituted C1-C20 alkyloxy groups; substituted or unsubstituted C6-C20 aryloxy groups; substituted or unsubstituted C6-C20 aryl C1-C20 alkyloxy groups; and halogen atoms;

each m independently represents an integer ranging from 0 to 4;

n is a number ranging from 5 to 500; and the substitution positions of the OH groups on the phenyl groups at both terminals of the molecule are each independently ortho, meta, or para position;

wherein the method comprises the steps of:

conducting hydrosilation reaction between a phenol compound substituted with an alkenyl group, represented by the following formula (IV):

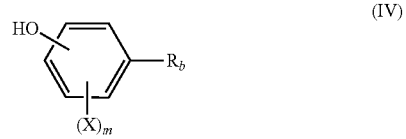

(IV)

wherein X and m are as defined above; $R_b$ represents an alkenyl group capable of producing the $R_a$ moiety defined above by the addition reaction with a polyorganohydrogensiloxane represented by formula (V):

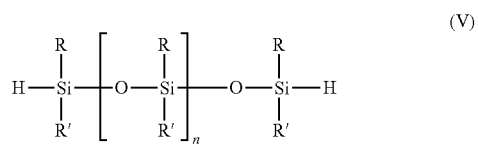

(V)

wherein R, R', and n are as defined above, in the presence of one or more platinum-based catalysts selected from the group consisting of chloroplatinic acid, complexes of platinum with vinylsiloxanes, and platinum-olefin complexes in an amount of more than 0.9 ppm as platinum metal; and reducing the platinum metal content of the resulting addition reaction product to 0.9 ppm or less by conducting one or more filtration procedures selected from the group consisting of filtration conducted where activated carbon is added, filtration conducted by using a filter comprising activated carbon, and filtration conducted by using a filter capable of adsorbing cations, alone or in combination.

12. The method of claim 11, wherein the phenol-modified polyorganosiloxane is represented by the following formula (III) and having a platinum metal content of 0.9 ppm or less:

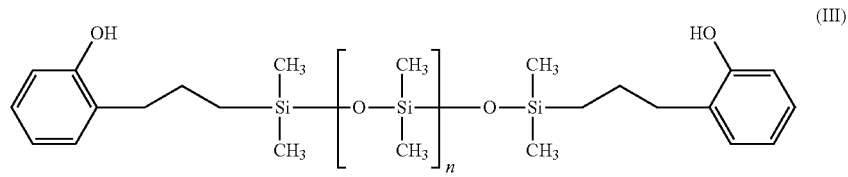

(III)

wherein n is a number ranging from 5 to 500.

13. The method of claim 11, when an unreacted compound of formula (IV) remains in the reaction product after conducting one or more filtration procedures selected from the group consisting of filtration conducted where activated carbon is added, filtration conducted by using a filter comprising activated carbon, and filtration conducted by using a filter capable of adsorbing cations, alone or in combination, further comprising a step of removing the unreacted compound of formula (IV) or reducing the amount thereof.

* * * * *